United States Patent [19]

Jamieson et al.

[11] 4,230,709
[45] Oct. 28, 1980

[54] METHOD OF TREATING ASTHMA WITH ALKYL, ALKYLIDENE AND ALKYLENE HYDANTOINS

[75] Inventors: William B. Jamieson, Woking; William J. Ross, Lightwater; Robin G. Simmonds, Wokingham; John P. Verge, Henley-on-Thames, all of England

[73] Assignee: Lilly Industries Limited, London, England

[21] Appl. No.: 39,074

[22] Filed: May 14, 1979

[30] Foreign Application Priority Data

May 23, 1978 [GB] United Kingdom ............... 21353/78

[51] Int. Cl.³ .................. A61K 31/445; A61K 31/415; C07D 471/04; C07D 233/58
[52] U.S. Cl. ............................... 424/256; 424/273 R; 424/45; 424/43; 546/121; 548/302; 548/308
[58] Field of Search ............................... 548/308, 302; 424/273 R, 256, 45, 43; 546/121

[56] References Cited

U.S. PATENT DOCUMENTS

| | | | |
|---|---|---|---|
| 2,225,384 | 12/1940 | Graenacher et al. | 548/308 |
| 2,527,366 | 10/1950 | Livak et al. | 548/308 |
| 2,541,101 | 2/1951 | Robinette et al. | 548/308 |
| 2,560,584 | 7/1951 | MacDonald | 548/308 |
| 3,395,153 | 7/1968 | Kitasaki et al. | 548/308 |
| 3,696,198 | 10/1972 | McCarty et al. | 424/273 R |

FOREIGN PATENT DOCUMENTS 48-29226 9/1973 Japan ..................................... 548/308

OTHER PUBLICATIONS

Elliott et al., J. Pharm. Pharmac., 1967, vol. 19, pp. 209-216.
Hazard et al. I., Chem. Abst., 1948, vol. 42, col. 7443.
Hazard et al. II, Compt. rend., 1950, vol. 230, pp. 243-245.
Hazard et al. III, Compt. rend., 1948, vol. 226, pp. 2018-2019.
Jones, Chem. Abst., 1961, vol. 55, col. 10471.
Jordan et al., J. Amer. Chem. Soc., 1949, vol. 71, p. 2258.
Ocaranza, Chem. Abst., 1962, vol. 57, col. 15783.
Sato, Chem. Abst., 1964, vol. 60, col. 2946.
U.S. Borax & Chem. Corp., Chem. Abst., 1968, vol. 69, No. 10439p.
Orazi et al. I, J. Chem. Soc., Perkin I, 1974, pp. 219-221.
Orazi et al. II, Tetrahedron, 1961, vol. 15, pp. 93-99.

Primary Examiner—Henry R. Jiles
Assistant Examiner—Richard A. Schwartz
Attorney, Agent, or Firm—James L. Rowe; Arthur R. Whale

[57] ABSTRACT

Pharmaceutical formulations are described, which comprise a hydantoin of formula (I):

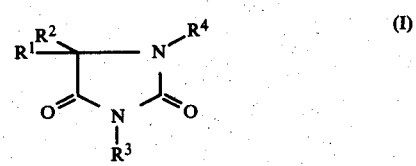

wherein $R^1$ is $C_{1-4}$ alkyl, $R^2$ is hydrogen or $C_{1-4}$ alkyl; or $R^1$ and $R^2$ taken together either represent a $C_{4-6}$ alkylene group or a group of formula:

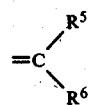

where
$R^5$ and $R^6$ independently represent hydrogen or $C_{1-4}$ alkyl;
$R^3$ is $C_{1-6}$ alkyl or benzyl;
$R^4$ is hydrogen or $C_{1-6}$ alkyl;
provided that $R^2$ and $R^4$ cannot both be hydrogen;
or $R^1$ and $R^4$ taken together represent a $C_{2-4}$ alkylene group;
associated with a pharmaceutically-acceptable carrier therefor. The compounds, some of which are novel, are useful in the treatment of immediate hypersensitivity diseases such as asthma.

2 Claims, No Drawings

METHOD OF TREATING ASTHMA WITH ALKYL, ALKYLIDENE AND ALKYLENE HYDANTOINS

This invention relates to heterocyclic compounds, more particularly to certain hydantoin derivatives which possess pharmacological activity. The invention also embraces processes for preparing novel compounds of the invention as well as pharmaceutical formulations and methods of treating mammals, including humans, susceptible to immediate hypersensitivity conditions such as asthma.

A number of alkyl substituted hydantoin derivatives are described in *Tetrahedron* 15, 93–99, (1961) and the *Journal of Chemical Society Perkin I*, 219–221 (1974) as intermediates or alkylated products with no associated teaching of pharmacological activity. The Applicants have now discovered that hydantoins of this type have useful pharmacological activity.

An object of the present invention is to provide compounds which have value in the prophylactic chemotherapy of asthma.

Accordingly, in the first aspect of the present invention there is provided a pharmaceutical formulation which comprises a hydantoin of formula (I):

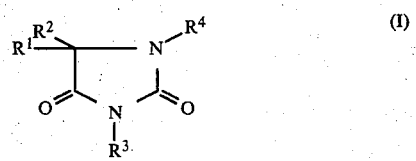

wherein
$R^1$ is $C_{1-4}$ alkyl, $R^2$ is hydrogen or $C_{1-4}$ alkyl;
or $R^1$ and $R^2$ taken together either represent a $C_{4-6}$ alkylene group or a group of formula:

where
$R^5$ and $R^6$ independently represent hydrogen or $C_{1-4}$ alkyl;
$R^3$ is $C_{1-6}$ alkyl or benzyl;
$R^4$ is hydrogen or $C_{1-6}$ alkyl;
provided that $R^2$ and $R^4$ cannot both be hydrogen;
or $R^1$ and $R^4$ taken together represent a $C_{2-4}$ alkylene group;
associated with a pharmaceutically-acceptable carrier therefor.

Compounds of formula (I) in which:
(A) $R^1$ and $R^2$ represent a group of formula:

(B) $R^4$ is $C_{1-6}$ alkyl with the exception of those compounds in which:
(a) $R^1$ is methyl, $R^2$ is hydrogen, $R^3$ is benzyl and $R^4$ is ethyl;
(b) $R^1$ and $R^2$ taken together represent —(CH$_2$)$_5$—, $R^3$ is methyl and $R^4$ is ethyl; or
(c) $R^1$ and $R^2$ are isopropyl, $R^3$ is methyl and $R^4$ is ethyl;
(C) $R^1$ and $R^4$ represent a $C_{2-4}$ alkylene group;
are novel and are provided in a further aspect of the invention.

Compounds in which $R^3$ is $C_{1-4}$ alkyl such as n-butyl are preferred.

Compounds of formula (I) can be prepared by the alkylation of a compound of formula (I) in which either or both of $R^3$ and $R^4$ is hydrogen.

The reagents and reaction conditions necessary to effect such alkylations will be well-known to those skilled in the art. However, it may be mentioned that this alkylation can be effected using an inert solvent such as dimethylformamide by generating the appropriate anion with a strong base such as sodium hydride and using an alkylating agent of formula $R^3X$ or $R^4X$ where X is a suitable leaving group such as a tosyl group or a radical such as bromide or iodide and where $R^3$ and $R^4$ are as previously defined.

The preparations of compounds of formula (I) in which $R^4$ is hydrogen is described in U.S. Pat. Nos. 3,395,153 and 3,696,198.

Compounds of formula (I) may also be prepared by the reaction of a compound of formula:

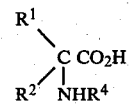

with an isocyanate of formula $R^3NCO$

This reaction can be effected by adding the isocyanate to a solution of the acid in an aqueous alkaline solution, such as aqueous caustic soda, followed by acidification with a strong mineral acid such as hydrochloric acid. This method is described in general terms by Dudley and Biss in the *Journal of Heterocyclic Chemistry* 10 173 (1973).

Compounds of formula (I) in which $R^1$ and $R^2$ together represent a group of formula:

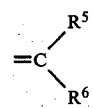

i.e. compounds of formula (II)

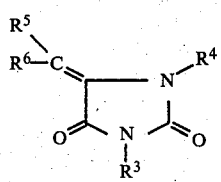

can be prepared by the dehydration of compounds of formula (III):

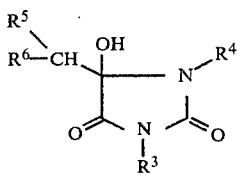

(III)

The dehydration can be effected using a strong concentrated acid such as sulphuric or methanesulphonic acid in an organic solvent such as toluene or benzene removing liberated water by azeotropic distillation. Compounds of formula (III) can be prepared using the method described in *Bulletin of the Chemical Society of Japan*, 39, 1559 (1966) to form the compound of formula (III) in which $R^3$ and $R^4$ are hydrogen followed by appropriate alkylation.

Compounds of formula (I) have been shown to be useful in the prophylactic treatment of immediate hypersensitivity diseases such as asthma in mammals. This activity has been demonstrated in guinea pigs using the "Herxheimer" test (*Journal of Physiology (London)* 117, 251 (1952)) at dosages of from 25 mg/kg to 200 mg/kg.

The compounds or compositions of the present invention may be administered by various routes, although oral administration is preferred, and for this purpose may be formulated in a variety of forms. Thus the compounds or compositions may be administered orally, rectally, topically or parenterally in the form of, for example, tablets, lozenges, sub-lingual tablets, sachets, cashets, elixirs, suspensions, suppositories, aerosols, ointments (for example, containing from 1 to 10% by weight of the active compound in a suitable base) soft and hard gelatin capsules, injection solutions and suspensions in physiologically acceptable media, and sterile packaged powders adsorbed onto a support material for making injection solutions.

Advantageously for this purpose, compositions may be provided in dosage unit form, preferably each dosage unit containing from 5 to 500 mg. (from 5.0 to 50 mg. in the case of parenteral administration, from 5.0 to 50 mg. in the case of inhalation and from 25 to 500 mg. in the case of oral or rectal administration) of a compound of formula I. Dosages of from 1 to 250 mg/kg preferably 1 to 20 mg/kg, per day of active ingredient may be administered although it will, of course, readily be understood that the amount of the compound or compounds of formula (I) actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The formulations of the present invention normally will consist of at least one compound of formula I mixed with a carrier, or diluted by a carrier, or enclosed or encapsulated by an ingestible carrier in the form of a capsule, sachet, cachet, paper or other container or by a disposable container such as an ampoule. A carrier or diluent may be any solid, semisolid or liquid material, which serves as a vehicle, excipient or medium for the active therapeutic substance.

Some examples of the diluents or carriers which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup B.P., methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and in the punch of the tabletting machine. For such purpose there may be employed for instance aluminum, magnesium or calcium stearate, talc or mineral oil.

The following non-limitative Examples illustrate the invention.

EXAMPLE 1

1-3-Di-n-butyl-5-methylhydantoin

Sodium hydride (1.44 g 0.03 mole) was suspended in dry dimethylformamide (50 ml) and 3-n-butyl-5-methylhydantoin (5.105 g 0.03 mole) added thereto. The mixture was heated, with stirring, at 50° C. for 1 hour after which time all the sodium hydride had reacted. The clear solution thus formed was cooled to room-temperature and excess n-butyl bromide (3.54 ml, 1.1 eq) in dimethylformamide (15 ml) was added and the mixture then heated for 3 hours and left at room-temperature overnight. The solution was concentrated to small volume under reduced pressure and the residue partitioned between 50% brine and ether. The ethereal extract was washed with brine, dried (Mg SO$_4$) and evaporated to dryness to yield an almost colourless oil which was distilled under reduced pressure to give the product as a colourless oil b.p. 79°–82° C. at 0.03–0.04 mm. Yield=5.8 g. (85%)

The following compounds were prepared in a similar manner using the appropriate hydantoin and alkyl halide.

EXAMPLE 2

1,5-Dimethyl-3-n-butylhydantoin, b.p. 68° C. at 0.03 mm.

EXAMPLE 3

1-Ethyl-3-n-butyl-5-methylhydantoin, b.p. 66° C. at 0.03 mm.

EXAMPLE 4

1-Hexyl-3-n-butyl-5-methylhydantoin, b.p. 80° C. at 0.02 mm.

EXAMPLE 5

3-Methyl-1,3-diazaspiro[4,5]decane-2,4-dione 1,3-diazaspiro[4,5]decane-2,4-dione (4.0 g 0.078 mole) *J. Prakt. Chem.* 141 5–43 (1934) was added to a suspension of sodium hydride (1.14 g 50% oil dispersion) in dimethylformamide and heated at 50° C. for 1 hour, cooled, methyl iodide added (1.63 ml. 1.1 eq) and the mixture heated at 50° C. The dimethylformamide was removed under reduced pressure and the residue partitioned between ethyl acetate and brine. The organic extract was washed with water, dried (MgSO$_4$), evaporated to dryness and the crystalline residue crystallised from ethyl acetate-light petroleum (40°–60° C.) to give the title compound as white prisms m.p. 214°–215° C. Yield 2.6 g=39%.

EXAMPLE 6

3-Benzyl-5,5-dimethyl-2,4-imidazolidine-dione 5,5-Dimethyl hydantoin (5.15 g, 0.039 mole) was added to a suspension of sodium hydride (1.87 g, 50% oil dispersion) in dry dimethylformamide (50 ml) and the mixture stirred and heated at 50° C. until evolution of hydrogen ceased. The solution was cooled and benzyl chloride (4.94 ml, 1.1 equivalents) was added and the mixture heated at 50° C. for 1½ hours. The dimethylformamide was removed under reduced pressure and the residue partitioned between ether and brine. The ethereal extracts were combined, washed with water, dried (MgSO$_4$) and the solvent evaporated to yield the title compound as a white crystalline solid m.p. 100°–102° C. Yield=8.0 g=91%.

EXAMPLE 7

3-n-Butyl-5,5-dimethylhydantoin n-Butyl isocyanate (9.5 g) was added dropwise to a stirred solution of α-aminoisobutyric acid (5.15 g) in aqueous sodium hydroxide (2.0 g. in 50 ml) at 0° C. during 2 hours. A small precipitate formed which was removed by filtration, the aqueous filtrate washed with ether (2×25 ml), acidified with concentrated hydrochloric acid (50 ml) and the mixture heated on the steam-bath for 30 minutes. The mixture was cooled and the product extracted into ether, the extract dried (MgSO$_4$) and evaporated to dryness to yield an oil (5.1 g). A further quantity (3 g) was obtained by continuous ether extraction of the aqueous layer for 2½ hours. The combined extracts were distilled in a Kugelrohr apparatus to give the title compound as a clear oil, b.p.=106° C. at 0.06 mm. Yield=7.8 g=85%.

EXAMPLE 8

2-n-Butyl-tetrahydro-1H-pyrrolo[1,2-c]imidazole-1,3-(2H)-dione

DL-Proline (2.5 g 0.0217 mole) was dissolved in water (20 ml) containing 2 N NaOH (10.9 ml, 0.0219 equiv) cooled to 0° C. and n-butyl isocyanate (3.27 g 0.33 mole) added dropwise to the stirred solution during 2 hours. The mixture was left at room-temperature overnight, filtered and washed with ether. The aqueous solution was acidified with concentrated hydrochloric acid (30 ml) and heated on the steam-bath for 30 minutes, cooled and continuously extracted with ether for 2 hours. Removal of the solvent gave a clear oil which was distilled under reduced pressure in a Kugelrohr apparatus to yield the product as a colourless oil, b.p. 90° C. at 0.02 mm. Yield 3.5 g=83%.

EXAMPLE 9

3-n-Butyl-5-methylenehydantoin 3-n-Butyl-5-methyl-5-hydroxyhydantoin (5.1 g 0.027 mole) was added to an ice-cold solution of 80% formic acid (50 ml) in acetic anhydride (60 ml) containing a small amount of hydroquinone (0.1 g) and the mixture heated on an oil-bath at 120° C. for 15 minutes. The mixture was then cooled to room-temperature and the solvents removed on the rotary evaporator under reduced pressure, yielding an oil which readily crystallised. The title product was crystallised from ethyl acetate-light petroleum (b.p. 40°–60° C.) to yield the product as prisms, m.p. 73° C. Yield=4.3 g=94%.

EXAMPLE 10

3-n-Butyl-5-(1-methylethylidene)-2,4-imidazolidine dione

5-Isopropylidenehydantoin (5.6 g 0.04 mole) *Journal of the Chemical Society,* 2265 (1955) was added to a stirred suspension of sodium hydride (2.0 g 50% dispersion-oil removed by washing with light petroleum) in dry dimethylformamide (50 ml) and the mixture then heated at 50° C. for 15 minutes after which time a cream coloured solid separated. The mixture was cooled to room-temperature, a solution of n-butyl bromide (6.0 g 0.044 mole) in dry dimethylformamide (25 ml) added and the mixture heated at 80° C. for 4 hours. The mixture was cooled to room temperature and evaporated to dryness in a rotary evaporator under reduced pressure. The residue was dissolved in water (200 ml) and extracted with ether (3×50 ml). The ethereal solution was dried (MgSO$_4$) and the solvent removed to yield a solid (6.6 g) which was crystallised from light petroleum (b.p. 60°–80° C.) to yield the title compound as needles, m.p. 130° C. Yield=4.3 g=55%.

EXAMPLE 11

1-Methyl-3-n-butyl-5-(1-methylethylidene)-2,4-imidazolidinedione 3-n-Butyl-5-(1-methylethylidene)-2,4-imidazolidinedione (3.8 g 0.02 mole) was added to a suspension of sodium hydride (0.95 g 50% oil dispersion 0.2 mole) in dry dimethylformamide (30 ml) and heated at 50° C. for five minutes. The mixture was cooled to room-temperature, methyl iodide (3.4 g 0.024 mole) added and the mixture heated at 50° C. for fifteen minutes. The mixture was then evaporated to dryness on a rotary evaporator under reduced pressure and the residue dissolved in water (100 ml) and extracted into ether (3×50 ml). The ethereal solution was dried (MgSO$_4$) the solvent removed and the residue (title compound) distilled under reduced pressure in a Kugelrohr apparatus, b.p. 100° C. at 0.01 mm. Yield=3.8 g=92%.

EXAMPLE 12

(Z)-1-Methyl-3-n-butyl-5-ethylideheydantoin (Z)-3-n-Butyl-5-ethylidenehydantoin (3.7 g 0.02 mole) was added to a suspension of sodium hydride (1.0 g 50% oil dispersion 0.02 mole-oil removed by washing with light petroleum b.p. 40°–60° C.) and the mixture heated at 50° C. for five minutes, cooled to room-temperature and methyl iodide (3.4 g 0.024 mole) added. Spontaneous reaction occurred and the mixture was then heated at 50° C. for fifteen minutes, cooled to room-temperature, evaporated to dryness under reduced pressure and the residue then suspended in water. The suspension was extracted with ether and the organic extract dried (MgSO$_4$). Removal of the solvent gave an oil which was distilled in a Kugelrohr apparatus to give the title compound as a clear oil, b.p. 92° C. at 0.02 mm. Yield=3.6 g=92%.

EXAMPLE 13

(Z)-3-n-Butyl-5-ethylidene-2,4-imidazolidinedione

A solution of (1' RS, 5 SR)-3-n-butyl-5-(1-hydroxyethyl)hydantoin (7.7 g 0.039 mole) in toluene (150 ml) containing methane sulphonic acid (2.5 mole 0.039 mole) was heated under a Dean and Stark apparatus for 48 hours during which time 0.65 ml of water collected (94% of theory). The mixture was cooled to room-temperature and washed with dilute sodium bicarbonate and dried (MgSO$_4$). Removal of the solvent gave a solid which was crystallised from cyclohexane to give the title compound as prisms m.p. 127° C. Yield = 3.3 g = 46.5%. The following Examples 14–20 illustrate pharmaceutical formulations containing the compound 3-n-butyl-5-methylenehydantoin.

EXAMPLE 14

Soft gelatin capsules were prepared using the following ingredients:

|  | Quantity (mg/capsule) |
| --- | --- |
| Active compound | 20 |
| Propyl gallate | 0.03 |
| Fractionated Coconut Oil B.P.C. | 70 |

The above ingredients were mixed and filled into soft gelatin capsules, the main shell components of which were gelatin and glycerine.

EXAMPLE 15

Hard gelatin capsules were prepared using the following ingredients:

|  | Quantity (mg/capsule) |
| --- | --- |
| Active compound | 25 |
| Silicon dioxide (fumed) | 25 |
| Lactose | 50 |
| Butylated hydroxyanisole B.P. | 0.02 |

The butylated hydroxyanisole was dissolved in the active ingredient and the solution so formed adsorbed onto the silicon dioxide (fumed). The lactose was then added and the whole mixed. Finally, the mixture was filled into hard gelatin capsules.

EXAMPLE 16

An ointment was made up from the following ingredients:

| Active compound | 2% by weight |
| --- | --- |
| Butylated hydroxyanisole B.P. | 0.04% by weight |
| White soft paraffin | q.s. 100% |

The hydroxyanisole was dissolved in the melted paraffin and the active compound then added in, and the mixture allowed to cool.

EXAMPLE 17

A topical cream containing 1% of the compound was prepared as follows:

|  | grams: |
| --- | --- |
| Active compound | 1 |
| Cetomacrogol 1000 | 3 |
| Cetostearyl alcohol | 10 |
| Liquid Paraffin | 7 |
| Butylated hydroxyanisole B.P. | 0.04 |
| Distilled Water | to 100.0 |

The active compound was mixed with the hydroxyanisole and suspended in the liquid paraffin. The cetostearyl alcohol was added and the mixture heated to 70° C. with stirring. The cetomacrogol 1000 was then dissolved in 60 g. of water heated to 70° C. The cetostearyl alcohol and liquid paraffin active compound mixture were then poured into the aqueous cetomacrogol 1000 solution with stirring and the stirring continued until the cream was cold. The cream was then made up to weight with water and passed through a stainless steel colloid mill set at a gap of 15/1000 inch.

EXAMPLE 18

Suppositories containing 30 and 60 mg. of the compound were prepared as follows:

| Active compound | 3 g |
| --- | --- |
| Henkel base | 97 g |

The active compound was mixed with the Henkel base which had been previously melted using the minimum amount of heat possible. The mixture was then poured into suppository moulds of a nominal capacity of 1 g. or 2 g. as desired, to produce suppositories each containing 25 mg. or 50 mg. of the active compound.

EXAMPLE 19

An aerosol was prepared containing the following ingredients:

|  | Quantity per ml. |
| --- | --- |
| Active compound | 10.00 mg. |
| Propylene glycol | 10.00 mg. |
| Dichlorotetrafluoroethane (Propellant 114) | 500 mg. |
| Dichlorodifluoromethane (Propellant 12) | 900 mg. |

The active compound was mixed with the propylene glycol and the mix added to the propellant 114, the mixture cooled to −15 to −20° C. and transferred to a filling device. At the same time a mixture of propellants 114 and 12, previously cooled to −15 to −20° C. was fed into a second filling device. A metered amount of propellant from the second filling device was introduced into a stainless steel container, followed by the required amount of material from the first filling device. The valve units were then fitted and sealed to the container. These valve units were equipped with metering device so that approximately 0.15 mg. of the active compound is released by a single actuation of the valve.

EXAMPLE 20

Tablets were prepared using the following components:

| Active compound | 15.00 mg. |
| --- | --- |
| Microcrystalline Cellulose | 240.00 mg. |
| Sodium Carboxymethyl Starch | 20.00 mg. |
| Magnesium Stearate | 2.5 mg. |
| Butylated Hydroxyanisole B.P. | 0.002 mg. |

The hydroxyanisole was dissolved in the active compound, the solution adsorbed onto the microcrystalline cellulose. This was mixed with the sodium carboxymethyl starch and the magnesium stearate then mixed in. Finally, the mixture was compressed to form tablets.

We claim:

1. A method of preventing an asthmatic attack in a mammal susceptible to asthmatic attacks which comprises administering an antiasthmatically effective amount of a compound of the formula:

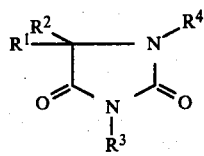

wherein $R^1$ is methyl, $R^2$ is hydrogen or methyl; or $R^1$ and $R^2$ taken together either represent a $C_{4-6}$ alkylene group or a group of formula:

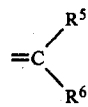

wherein
$R^5$ and $R^6$ independently represent hydrogen or methyl;
$R^3$ is $C_{1-6}$ alkyl or benzyl;
$R^4$ is hydrogen or $C_{1-6}$ alkyl;
provided that $R^2$ and $R^4$ cannot both be hydrogen;
or $R^1$ and $R^4$ taken together represent a $C_{2-4}$ alkylene group, associated with a pharmaceutically-acceptable carrier therefor.

2. A method according to claim 1 in which the antiasthmatically-effective drug is administered to a human susceptible to asthmatic attacks.

* * * * *